(12) United States Patent
Chang et al.

(10) Patent No.: US 10,167,448 B2
(45) Date of Patent: Jan. 1, 2019

(54) PHARMACEUTICAL COMPOSITION FOR TREATING CEREBROVASCULAR DISEASES, CONTAINING STEM CELL-DERIVED EXOSOME AS ACTIVE INGREDIENT

(71) Applicant: SAMSUNG LIFE PUBLIC WELFARE FOUNDATION, Seoul (KR)

(72) Inventors: Yun Sil Chang, Seoul (KR); Won Soon Park, Seoul (KR); Dong Kyung Sung, Seoul (KR); So Yoon Ahn, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 190 days.

(21) Appl. No.: 15/103,663

(22) PCT Filed: Dec. 12, 2014

(86) PCT No.: PCT/KR2014/012289
§ 371 (c)(1),
(2) Date: Jun. 10, 2016

(87) PCT Pub. No.: WO2015/088286
PCT Pub. Date: Jun. 18, 2015

(65) Prior Publication Data
US 2016/0310534 A1    Oct. 27, 2016

(30) Foreign Application Priority Data
Dec. 12, 2013    (KR) ........................ 10-2013-0154891

(51) Int. Cl.
| C12N 5/0775 | (2010.01) |
| A61K 35/28 | (2015.01) |
| A61K 35/545 | (2015.01) |
| A61K 9/00 | (2006.01) |
| A61K 35/51 | (2015.01) |

(52) U.S. Cl.
CPC .......... *C12N 5/0665* (2013.01); *A61K 9/0019* (2013.01); *A61K 35/28* (2013.01); *A61K 35/51* (2013.01); *A61K 35/545* (2013.01); *C12N 2501/734* (2013.01)

(58) Field of Classification Search
None
See application file for complete search history.

(56) References Cited

U.S. PATENT DOCUMENTS

| 2002/0106780 A1* | 8/2002 | Fiscella ................. C07K 14/47 435/226 |
| 2006/0084082 A1* | 4/2006 | Ruben ................. C07K 14/47 435/6.16 |
| 2009/0131315 A1* | 5/2009 | Vitek ................. A61K 38/1709 514/5.4 |
| 2010/0047351 A1* | 2/2010 | Zeitlin ................. A61K 35/50 424/484 |
| 2010/0124569 A1* | 5/2010 | Abbot ................. A61K 35/50 424/484 |
| 2012/0014921 A1* | 1/2012 | Kramer ................. A61K 35/30 424/93.2 |
| 2013/0273011 A1 | 10/2013 | Ichim et al. ........... A61K 35/28 |
| 2014/0056842 A1* | 2/2014 | Sackner-Bernstein ...................... A61K 38/18 424/85.1 |
| 2015/0045298 A1 | 2/2015 | Bang et al. ............ A61K 35/28 |

FOREIGN PATENT DOCUMENTS

| JP | 2002-535665 | 10/2002 | ............. G01N 30/88 |
| JP | 2006-509516 | 3/2006 | ............... C12N 5/06 |
| JP | 2007-535947 | 12/2007 | ............... C12N 5/06 |
| KR | 2005-0088118 | 9/2005 | ............... C12N 5/06 |
| KR | 10-2012-0088778 | 8/2012 | ............. A61K 35/44 |
| WO | WO 2012/125471 | 9/2012 | ............. A61K 35/28 |
| WO | WO 2012-125471 | 9/2012 | ............. A61K 35/28 |
| WO | WO 2013/039000 | 3/2013 | ............. A61K 35/12 |
| WO | WO 2013/102219 | 7/2013 | ............. C12N 5/073 |
| WO | WO 2013/150303 | 10/2013 | ........... A61K 31/711 |
| WO | WO 2014/013258 | 1/2014 | ........... A61K 31/711 |
| WO | WO 2014013258 | * 1/2014 | |

OTHER PUBLICATIONS

Denzer et al. Journal of Cell Science 113, 3365-3374 (2000).*
Fukuda et al. Genes 2013, 4, 435-456.*
Extended European Search Report from corresponding European Application No. 14869537.2 dated Apr. 21, 2017.
Extended European Search Report from corresponding European Application No. 14868825.2 dated Jul. 7, 2017.
Office Action from corresponding Japanese Application No. 2016-539061 dated Mar. 21, 2017.
Aharon A., et al.; "Microparticles, thrombosis and cancer", 2008 Elsevier Ltd.
Ruenn Chai Lai, et al.; "Mesenchymal stem cell exosome: a novel stem cell-based therapy for cardiovascular disease", Regen. Med., 2011, 6(4), 481-492.
Xin, H. et al.; "System administration of exosomes released from mesnchymal stromal cells promote functional recovery and neurovascular plasticity after stroke in rats", Journal of Cerebral Blood Flow & Metabolism (2013) 33, 1711-1715.

(Continued)

*Primary Examiner* — Julie Wu
*Assistant Examiner* — Douglas F White
(74) *Attorney, Agent, or Firm* — Harness, Dickey & Pierce, P.L.C.

(57) ABSTRACT

The present invention relates to a pharmaceutical composition for treating cerebrovascular diseases including stem cell-derived exosomes as an active ingredient. The stem cell-derived exosomes according to the present invention have superior nerve cell protective effects, such as inhibition of cerebral ventricular distention, reduction of hydrocephalus, and inhibition of nerve cell death and cellular inflammation in an intraventricular hemorrhage (IVH) animal model, and thus, can be useful in treating cerebrovascular diseases including intraventricular hemorrhage, etc.

5 Claims, 16 Drawing Sheets

(56) References Cited

OTHER PUBLICATIONS

Journal of Cerebral Blood Flow & Metabolism, (2013), vol. 33, pp. 1711-1715.
Stroke: So Yoon Ahn, MD et al, "Mesenchymal Stem Cells Prevent Hydrocephalus After Severe Intraventricular Hemorrhage" (2013), vol. 44, pp. 497-504.
International Search Report (ISR) dated Mar. 25, 2015 in PCT/KR2014/012289 published as WO 2015/088286 with English Translation.
Mahmood, A., et al. (2004). "Intravenous administration of marrow stromal cells (MSCs) increases the expression of growth factors in rat brain after traumatic brain injury" *Journal of Neurotrauma.* 21(1):33-39.
Teixeira, F.G. et al., "Mesenchymal stem cells secretome: a new paradigm for central nervous system regeneration?" *Cellular and Molecular Life Sciences*, 70(20):3871-3882.
Xin, H. et al., (2013). "Systematic administration of exosomes released from mesenchymal stromal cells promote functional recovery and neurovascular plasticity after stroke in rats" *Journal of Cerebral Blood Flow & Metabolism.* 33(11):1711-1715.

* cited by examiner

PHARMACEUTICAL COMPOSITION FOR TREATING CEREBROVASCULAR DISEASES, CONTAINING STEM CELL-DERIVED EXOSOME AS ACTIVE INGREDIENT

CROSS-REFERENCE TO RELATED APPLICATIONS

This application is a national phase application of PCT Application No. PCT/KR2014/012289, filed on Dec. 12, 2014, which claims the benefit and priority to Korean Patent Application No. 10-2013-0154891, filed Dec. 12, 2013. The entire disclosures of the applications identified in this paragraph are incorporated herein by references.

FIELD

The present invention relates to a pharmaceutical composition for treating cerebrovascular diseases including stem cell-derived exosomes as an active ingredient.

BACKGROUND

Stem cells are undifferentiated cells having the ability to differentiate into two or more cell types with self-replication ability. Stem cells can be classified into totipotent stem cells, pluripotent stem cells, and multipotent stem cells depending upon differentiation potency thereof. In addition, stem cells can be classified into embryonic stem cells and adult stem cells depending upon biological origin. While embryonic stem cells are derived from preimplantation embryos, fetal reproductive organs in various stages of development, and the like, adult stem cells are derived from each organ, e.g., bone marrow, brain, liver, pancreas, or the like, of adults.

Recently, preclinical and clinical research to apply stem cells to various diseases, such as cerebral infarctions, traumatic brain injuries, and musculoskeletal diseases, is underway. However, current technology is merely focused on simply isolation, culture/proliferation and injection of stem cells. In addition, recent clinical research results show that such stem cell therapies do not exhibit distinct effects yet. Accordingly, research on various gene-modified stem cells to increase therapeutic effects is underway. However, application of cell therapy, in which genes are modified, to the human body is limited due to ethical problems.

In addition, there are several problems in applying therapeutic methods using stem cells to clinical trials. For example, tumor masses may be formed after engraftment of stem cells to organs, and cerebral infarction may occur due to an artery occlusion likely induced by the large size of stem cell itself. The stem cells easily move into the brain when the brain-blood vessel barrier is open as in an acute phase. However, in a chronic phase, movement of the stem cells is limited due to large sizes thereof.

Meanwhile, cerebrovascular diseases are neurologic deficits due to a problem in blood supply to the brain. Examples of cerebrovascular diseases include stroke, cerebral infarction, cerebral hemorrhage, cerebral arteriosclerosis, subarachnoid hemorrhage, cerebral thrombosis, cerebral embolism, etc.

Recently, a low birthrate is one of the most serious national problems. With regard to this, delivery of premature babies due to an increase in the average age of pregnant women and the application of the assisted reproductive technique due to increased infertility are remarkably increasing. The most important factor determining the quality of life of premature babies is a cranial nerve development state after treatment. With regard to this, intraventricular hemorrhage (IVH) in premature infants generally occurs within one week after birth and is a most important and dangerous disease that causes severe diseases including cerebral palsy, mental retardation, hearing loss, vision loss, and the like, as well as hydrocephalus, after bleeding. Bleeding into the cerebral ventricle causes damage to neighboring immature brain tissue and hydrocephalus after bleeding, thereby causing severe brain damage. However, there is, as yet, no definite remedy for intraventricular hemorrhage, and thus, it is a very important and urgent task to develop a remedy for treating premature babies.

Although research to develop drugs for treating cerebrovascular diseases has been actively underway, there is, as yet, no absolutely disclosure about a relation between cerebrovascular diseases, particularly the intraventricular hemorrhage, and stem cell-derived exosomes.

DISCLOSURE

Technical Problem

The present inventors have continued research to develop a novel drug for treating cerebrovascular diseases and, as a result of such research, confirmed that stem cell-derived exosomes have superior cerebrovascular disease therapeutic effects, such as inhibition of cerebral ventricular distention, nerve cell death, and cellular inflammation in the intraventricular hemorrhage animal models, thus completing the present invention.

Accordingly, it is an object of the present invention to provide a pharmaceutical composition for treating cerebrovascular diseases including stem cell-derived exosomes as an active ingredient.

Technical Solution

The above and other objects can be accomplished by the provision of a pharmaceutical composition for treating cerebrovascular diseases including stem cell-derived exosomes as an active ingredient.

Advantageous Effects

The stem cell-derived exosomes according to the present invention have remarkable nerve cell protective effects such as the inhibition of ventricular enlargement, decrease in hydrocephalus, and inhibition of nerve cell death and cellular inflammation in an intraventricular hemorrhage (IVH) animal model, and thus can be useful in treating cerebrovascular diseases including IVH and the like.

MODES OF THE INVENTION

Figure 1:
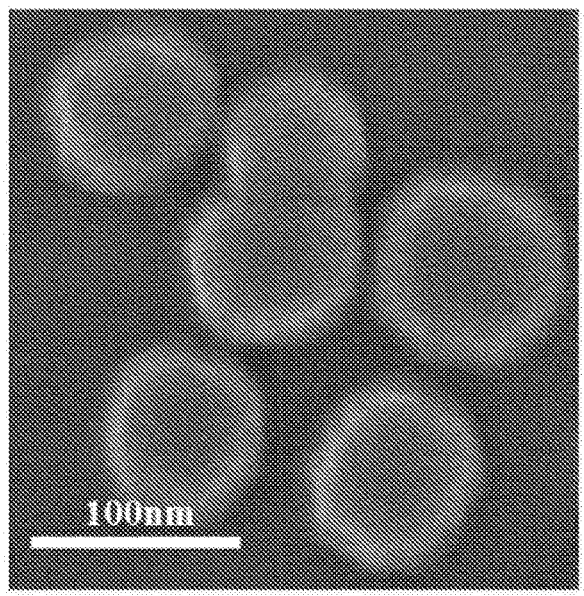
FIG. 1 illustrates the shapes of stem cell-derived exosomes isolated according to the present invention, confirmed by SEM image analysis.

Hereinafter, the present invention will be described in detail.

The present invention provides a pharmaceutical composition for treating cerebrovascular diseases including stem cell-derived exosomes as an active ingredient.

In the present invention, the term "stem cells" refers to undifferentiated cells having the ability to differentiate into two or more different cell types, along with self-replication ability.

The stem cells of the present invention may be autologous or allogeneic stem cells and may be derived from any animal including humans and non-human mammals. In addition, the stem cells may be derived from, without being limited to, adults or embryos.

The stem cells of the present invention include embryonic stem cells or adult stem cells, preferably, adult stem cells. The adult stem cells may be, without being limited to, mesenchymal stem cells, human tissue-derived mesenchymal stromal cells, human tissue-derived mesenchymal stem cells, multipotent stem cells, or amniotic epithelial cells, preferably, mesenchymal stem cells. The mesenchymal stem cells may be derived from, without being limited to, the umbilical cord, cord blood, bone marrow, fat, muscle, nerve, skin, amnion, placenta, etc.

In the present invention, the term "exosomes" refers to small vesicles having a membrane structure secreted from various cells. Exosomes have diameters of about 30 to 100 nm, and fusion between plasma membranes and multivesicular bodies occurs, thereby being released to the outside of the cells.

In the present invention, the term "cerebrovascular disease" includes stroke, cerebral infarction, cerebral hemorrhage, cerebral arteriosclerosis, subarachnoid hemorrhage, cerebral thrombosis, or cerebral embolism. The cerebral hemorrhage is preferably intraventricular hemorrhage (IVH), but the present invention is not limited thereto.

The stem cell-derived exosomes according to the present invention have superior nerve cell protective effects such as inhibition of cerebral ventricular distention, reduction of hydrocephalus, and inhibition of nerve cell death and cellular inflammation in an intraventricular hemorrhage (IVH) animal model.

Accordingly, the stem cell-derived exosomes according to the present invention are useful in treating cerebrovascular diseases including the intraventricular hemorrhage, etc.

A composition of the present invention may further include one or more publicly known active ingredients having cerebrovascular disease treatment effects, along with stem cell-derived exosomes.

The composition of the present invention may be formulated into a medicine having a unit dosage form suitable for being administrated into the body of a subject according to a general method used in the pharmaceutical field. As preferred examples of formulations for parenteral administration suitable for accomplishing such a purpose, there are injection agents such as an ampule for injection, infusion agents such as an infusion bag, spraying agent such as an aerosol formulation, and the like. The ampule for injection may be mixed with an injectable solution immediately before use. The injectable solution may be a saline solution, glucose, Ringer's solution, or the like. In addition, the infusion bag may be made of polyvinyl chloride or polyethylene.

The composition of the present invention may further include a suitable carrier generally used to prepare pharmaceutical compositions. For example, a formulation for injection may further include a preservative, an agent for relieving pain upon injection, a solubilizer, a stabilizer, etc. and a formulation for topical administration may further include a base, a vehicle, a lubricant, a preservative, etc.

The composition of the present invention may be administrated through various paths. All paths for administration may be anticipated. For example, the composition may be administrated by oral, rectal, intravenous, intramuscular, subcutaneous, intrauterine dura mater, or cerebrovascular injection. Preferably, the exosomes may be directly engrafted to or transplanted into the cerebral ventricle of a subject requiring treatment, but the present invention is not limited thereto.

The composition of the present invention may be used alone or in combination with surgery, radiation therapy, hormone therapy, chemotherapy, and a biological reaction controller, to treat cerebrovascular diseases.

In addition, the present invention provides a method of treating a cerebrovascular disease of a subject by administrating the stem cell-derived exosomes in a pharmaceutically effective amount.

It will be easily understood by those skilled in the art that the pharmaceutically effective amount can be determined by a caregiver in the accurate medical judgment range. A pharmaceutically effective amount specific to a particular subject preferably depends upon the types and degrees of reactions to be accomplished, formulation types dependent upon cases, particular composition types, the age, weight, general health conditions, gender, and diet of a subject to be treated, administration time, administration paths, a secretion rate of the composition, treatment periods, drug types used with the particular composition or simultaneously therewith, various factors, and similar factors well known in the field of medicine.

Hereinafter, the present invention will be described in more detail with reference to the following preferred examples. However, it should be understand that the following examples are merely to concretely explain the spirit of the invention and therefore, there is no intent to limit the invention to the examples Example 1. Isolation of Stem Cell-Derived Exosomes To isolate stem cell-derived exosomes, an ultracentrifuge was used. More particularly, mesenchymal stem cells were diluted to a concentration of $1\times10^5$ cells/ml and then aliquoted into 3 ml portions in 60 mm culture plates, followed by culturing for one week. When the cells were cultured to confluence in the culture plate, a medium thereof was changed with a new culture medium including thrombin at concentration of 50 U/ml in the medium, followed by culturing for 24 hours. Subsequently, the culture medium was aliquoted into 2 ml centrifugation tubes, followed by centrifuging at 4° C. and 10,000 g for 30 minutes. Supernatants were transferred to new tubes to remove cell debris. The supernatants were again ultracentrifuged at 4° C. and 100,000 g for two hours. Supernatants were removed and exosomes were isolated.

Exosomes isolated according to the process were observed by SEM imaging. Expressions of CD63 and CD9 (System Bioscience, Mountain View, Calif., USA), as exosome markers, were investigated by Western blotting. In addition, exosome membranes were lysed with a lysis buffer and then proteins in exosomes were isolated. The amounts of HGF and VEGF, as growth factors, in the exosomes were measured using Procarta immunoassay kit (Affymetrix, Santa Clara, Calif., USA). Results are respectively illustrated in FIGS. 1 to 3.

As illustrated in FIG. 1, it can be confirmed that exosomes obtained according to the aforementioned method have normal globular shapes having a diameter of about 100 nm.

Figure 2:
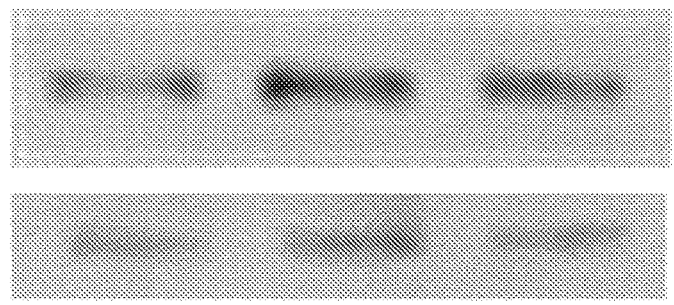
FIG. 2 illustrates normal expressions of CD63 and CD9, as exosome markers, in stem cell-derived exosomes isolated according to the present invention.
Figure 3:
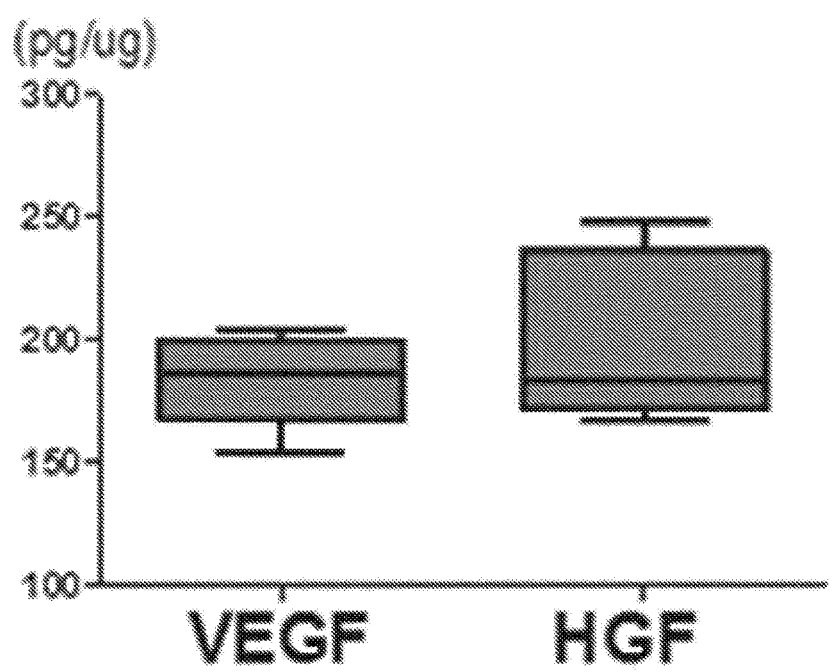
FIG. 3 illustrates normal expressions of VEGF and HGF, as growth factors, in stem cell-derived exosomes isolated according to the present invention.

In addition, as illustrated in FIGS. 2 and 3, it can be confirmed that exosomes obtained according to the aforementioned method normally express CD63 and CD9, as exosome markers, and VEGF and HGF, as growth factors, are present in the exosomes.

Example 2. Investigation of Nerve Cell Protective Effects of Stem Cell-Derived Exosomes To investigate in vitro nerve cell protective effects of stem cell-derived exosomes obtained according to Example 1, the following experiments were conducted.

2-1. Determination of Thrombin Treatment Concentration

A rat fetus was sacrificed at 18.5 days' gestation. The cerebral cortex of the fetus was separated and then nerve cells therefrom were cultured for seven days. Death of the cultured nerve cells was induced by varying thrombin treatment concentrations (10 to 80 U/ml) and time (8 or 16 hours). Cell viability was measured using a cell count kit (Dojindo, Kumamoto, Japan). Results are illustrated in FIG. 4.

Figure 4:
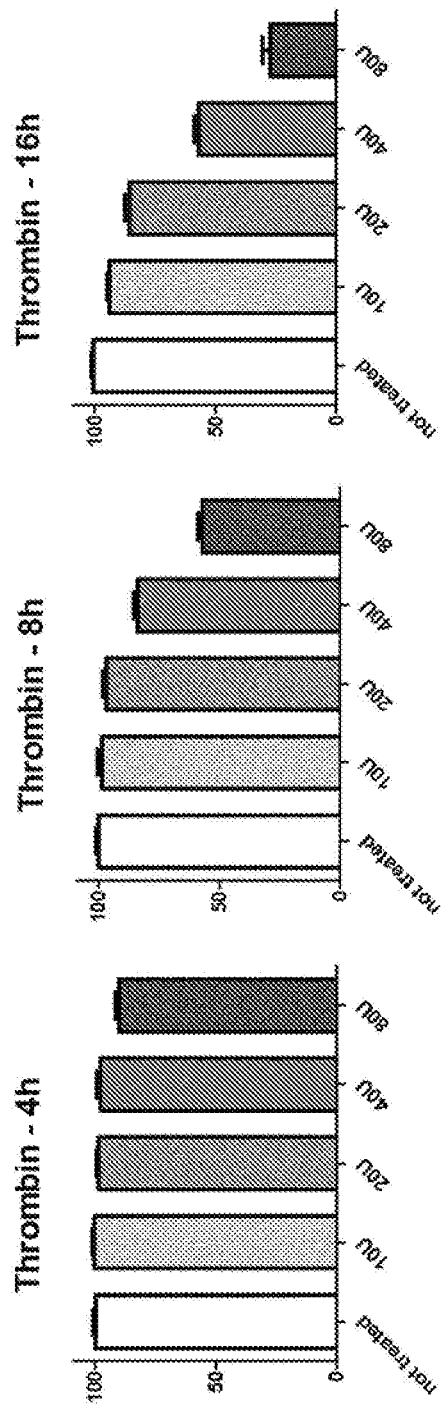
FIG. 4 illustrates the viability of nerve cells dependent upon treatment concentration and time of thrombin, when nerve cells are treated with thrombin.

As illustrated in FIG. 4, it can be confirmed that, when nerve cells are treated with thrombin at a concentration of 80 U/ml for eight hours or at a concentration of 40 U/ml for 16 hours, the survival rate of the nerve cells is about 50%. Subsequent experiments were conducted using these two conditions.

2-2. Investigation of Nerve Cell Protective Effects

Thrombin treatment was performed in the same manner as in Example 2-1 in order to induce nerve cells death. Death-induced nerve cells were treated with 1 ml of stem cell-derived exosomes obtained according to Example 1, at a concentration of 15 µg/ml. Subsequently, cell viability was measured using a cell count kit. Results are illustrated in FIGS. 5 and 6.

Figure 5:
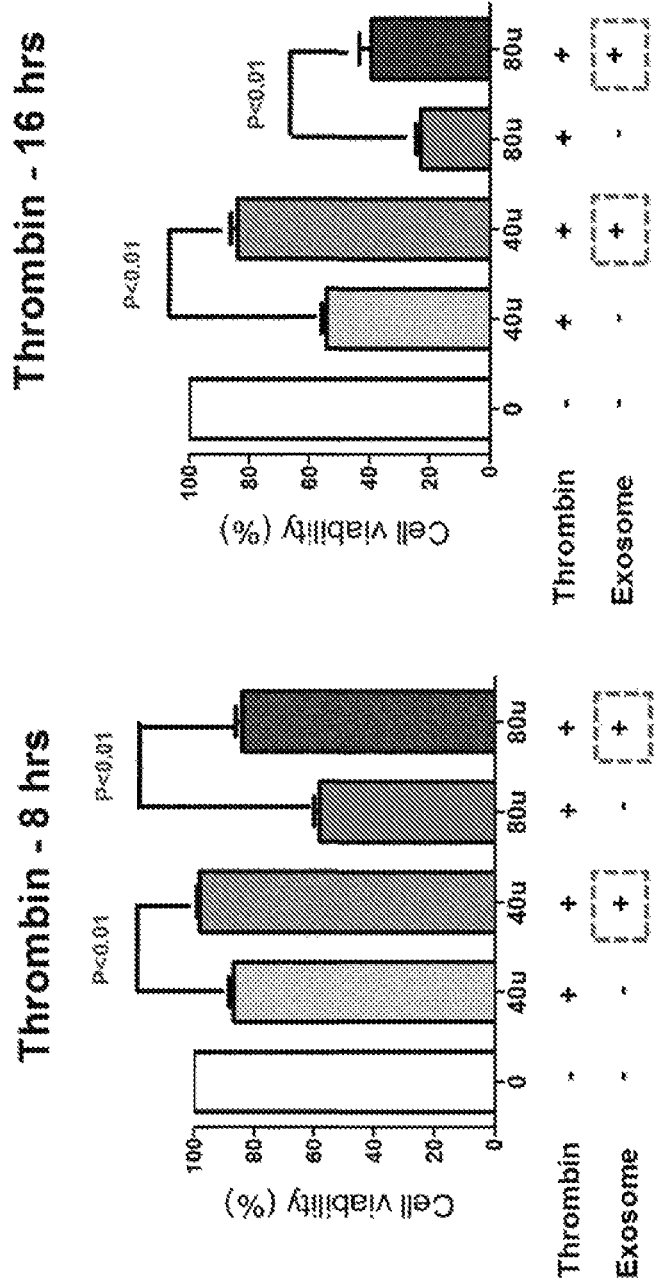
FIG. 5 illustrates the viability of nerve cells treated with thrombin and then with stem cell-derived exosomes according to the present invention.
Figure 6:
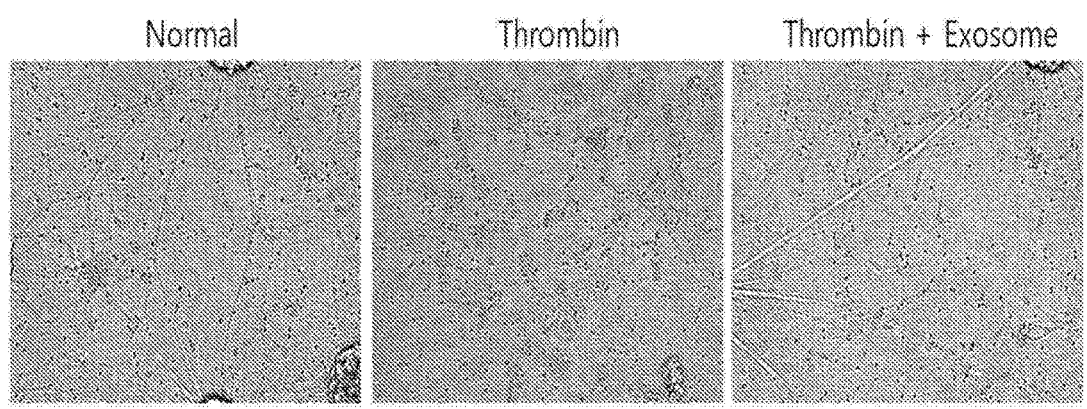
FIG. 6 illustrates the shapes of nerve cells treated with thrombin and then with stem cell-derived exosomes according to the present invention.

As illustrated in FIGS. 5 and 6, it can be confirmed that, when the nerve cells death-induced by the treatment of thrombin are treated with the stem cell-derived exosomes according to the present invention, nerve cell death is remarkably inhibited. From these results, it can be confirmed that the stem cell-derived exosomes have protective effects for nerve cells.

Example 3. Investigation of Therapeutic Effects of Stem Cell-Derived Exosomes in Intraventricular Hemorrhage Animal Models To investigate the in vivo cerebrovascular disease therapeutic effects of stem cell-derived exosomes obtained according to Example 1, the following experiments were conducted.

3-1. Designs of Intraventricular Hemorrhage Animal Models and Experiments

Figure 7:
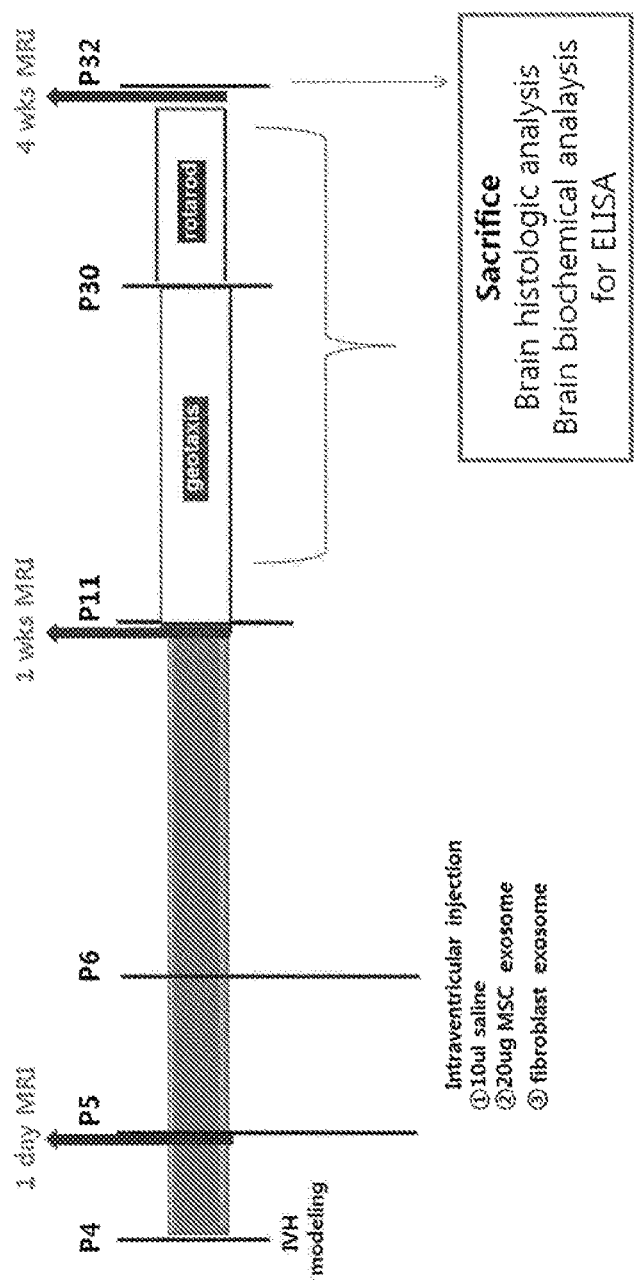
FIG. 7 illustrates an animal experiment design to investigate the intraventricular hemorrhage therapeutic effects.

Male SD rats (Sprague-Dawley rats, Orient Co, Seoul, Korea) were used as experimental animals. Experiments were conducted from 4 days (P4) to 32 days (P32) after birth. To induce the intraventricular hemorrhage (IVH), rats at P4 were anesthetized with 1.5% to 2% isoflurane. Subsequently, 200 µl of blood collected from the caudal veins of mother rats was slowly administered into both cerebral ventricles (100 µl of the blood was administrated to each of right and left cerebral ventricles) according to a stereotaxic guidance (Digital Stereotaxic Instrument with Fine Drive, MyNeurolab, St. Louis, Mo.; coordinates: x=±0.5, y=+1.0, z=+2.5 mm relative to bregma). In the case of a control group (NC), the same surgery was conducted without blood administration. One day after IVH induction, the brains of rats at five days (P5) after birth were photographed by means of 7-teslar MRI to investigate that intraventricular hemorrhage was normally induced. At two days after IVH induction, rats at six days (P6) after birth were anesthetized with 1.5% to 2% isoflurane and then saline (IC), 20 µg of mesenchymal stem cell-derived exosomes (IM exo), or 20 µg of fibroblast-derived exosomes (IF exo) was slowly administrated into the right cerebral ventricle of each rat. At 7 and 28 days (P11 and P32) after IVH induction, brain MRI images of rats were generated. At 28 days after IVH induction, the rats were sacrificed and the brain tissues thereof were analyzed. A more particular experimental design is illustrated in FIG. 7.

3-2. Brain MRI Image Analysis

The brain MRI images of the rats obtained at 1, 7 and 28 days after IVH induction were analyzed. The degree of cerebral ventricular distention was analyzed using an Image J program and the volume of each of the cerebral ventricles/total brain volume was found. Results are illustrated in FIGS. 8 and 9.

Figure 8:
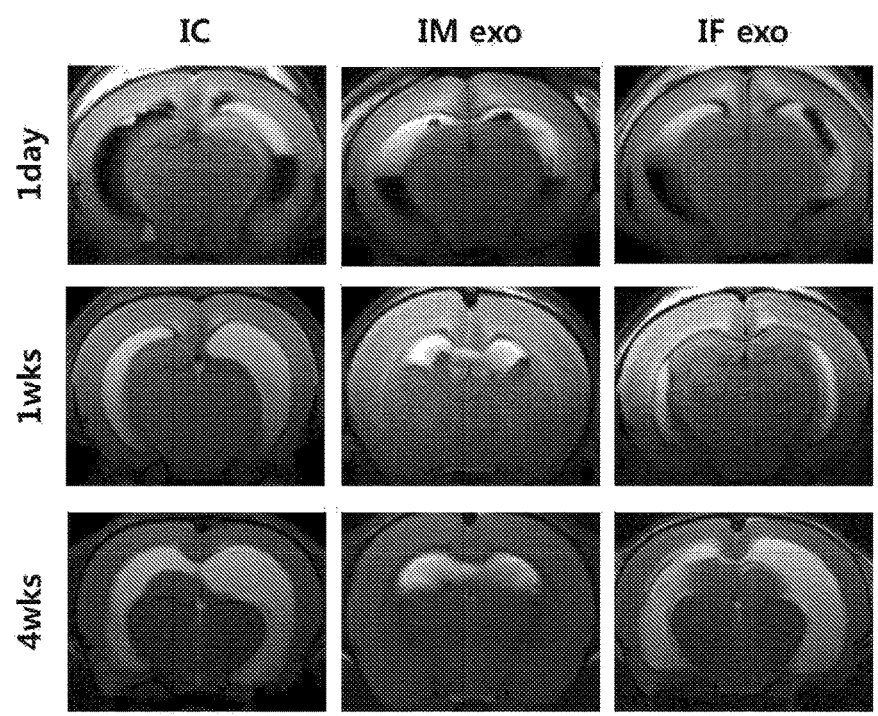
FIG. 8 illustrates the degree of cerebral ventricular distention 1, 6 and 28 days after IVH induction, through brain MRI image analysis.
Figure 9:
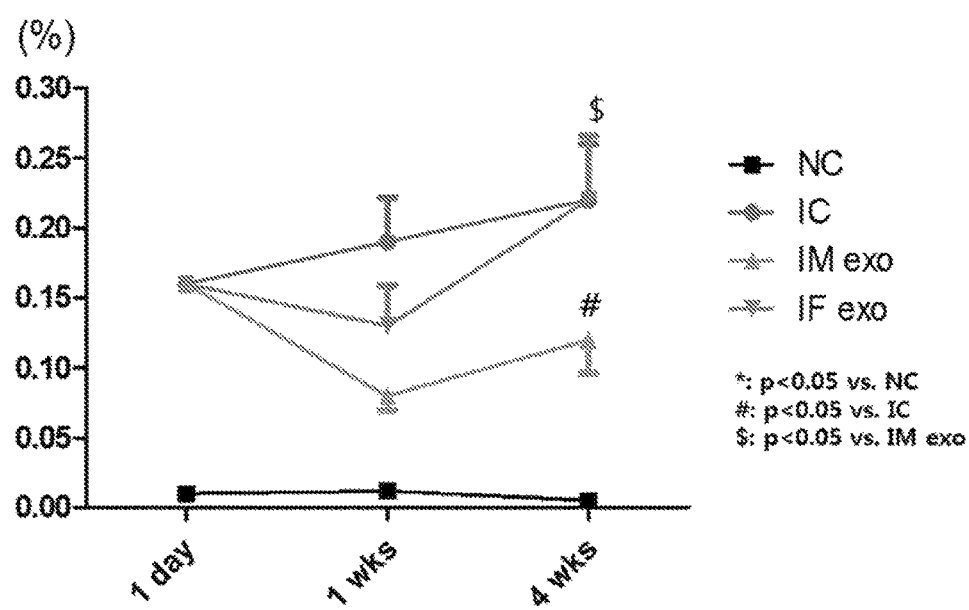
FIG. 9 illustrates the volume of each of cerebral ventricles/total brain volume 1, 6 and 28 days after IVH induction, through brain MRI image analysis.

As illustrated in FIGS. 8 and 9, it can be confirmed that, while the cerebral ventricles of the rats are distended and hydrocephalus is induced by IVH induction, the hydrocephalus is remarkably reduced in the group to which the mesenchymal stem cell-derived exosomes were administrated. Meanwhile, there is no significant difference between the group, to which the fibroblast-derived exosomes were administrated, and the IVH-induced group (IC).

3-3. Sensorimotor Behavior Evaluation

Negative geotaxis evaluation was performed by recording the time taken, after downwardly placing the head of a rat on a slanted board, until a head of the rat faces upward on the slanted board, according to a conventionally known method. The evaluation was conducted at each of P11, P18, P25, and P32. In addition, so as to analyze influence on long-term motor functions, the rotarod evaluation was continuously conducted at P30 to P32 according to a conventionally known method. Results are respectively illustrated in FIGS. 10 and 11.

Figure 10:
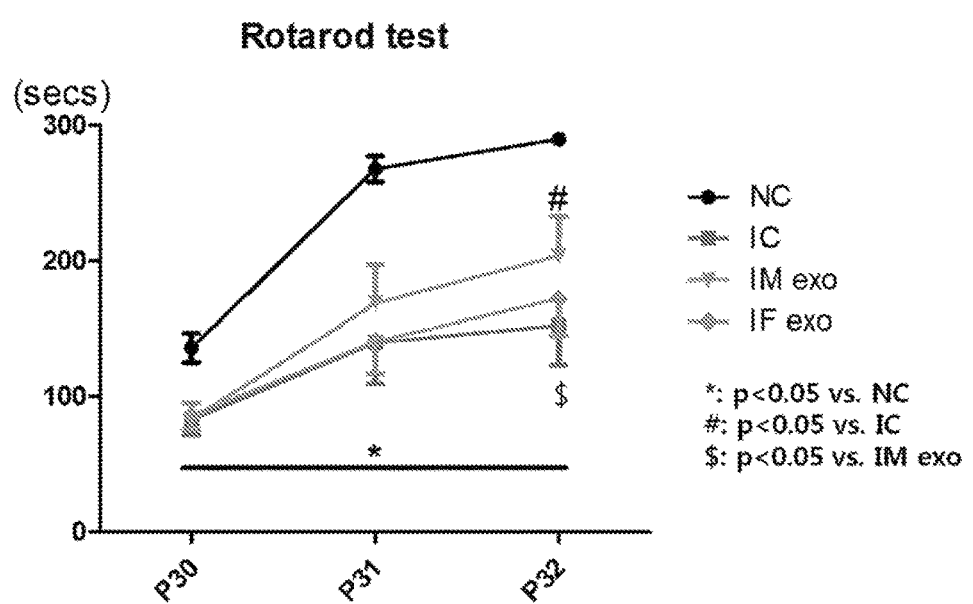
FIG. 10 illustrates negative geotaxis evaluation results in intraventricular hemorrhage animal models.
Figure 11:
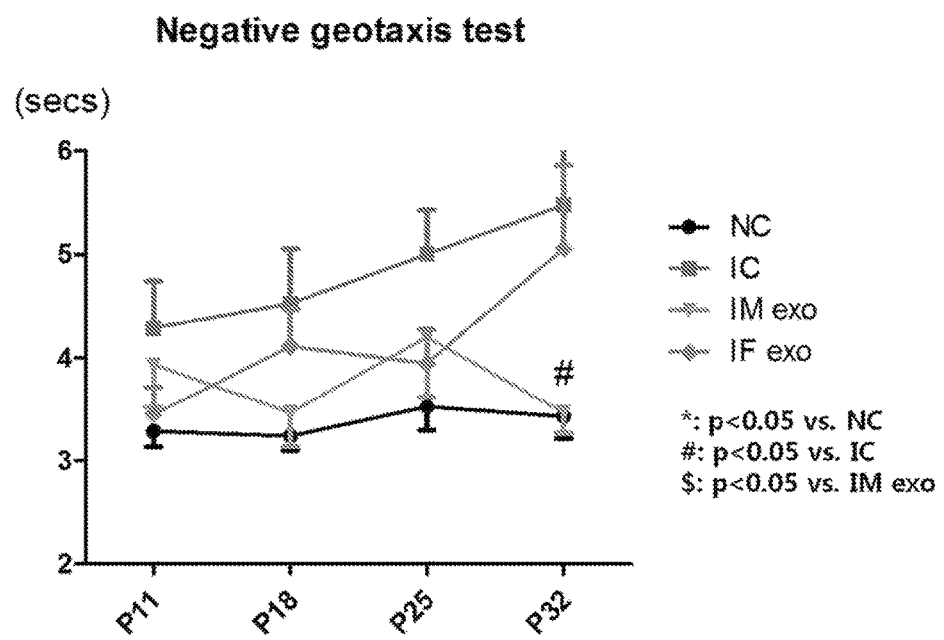
FIG. 11 illustrates rotarod evaluation results obtained using intraventricular hemorrhage animal models.

As illustrated in FIGS. 10 and 11, the IVH-induced group shows significantly damaged sensorimotor function, compared to the control group. But, the group, to which the mesenchymal stem cell-derived exosomes were administrated, shows improved effects in both the negative geotaxis and rotarod evaluations.

3-4. Analysis of Cell Death Degrees

After terminating the experiments, the brains of the rats were isolated and embedded in paraffin. Brain tissue specimens were prepared by cutting a 4 µm thick paraffin film. To investigate cellular death of periventricular white matter, an immunofluorescence assay was performed using the terminal deoxynucleotidyl transferase-mediated deoxyuridine triphosphate nick-end labeling (TUNEL) technique (kit S7110 ApopTag, Chemicon, Temecula, Calif.). Here, three coronal sections of brain, bregma +0.95 mm to −0.11 mm were randomly selected. Each of the randomly selected sections was examined three times by means of a microscope and an average value thereof was found to perform statistical analysis. Results are illustrated in FIG. 12.

Figure 12:
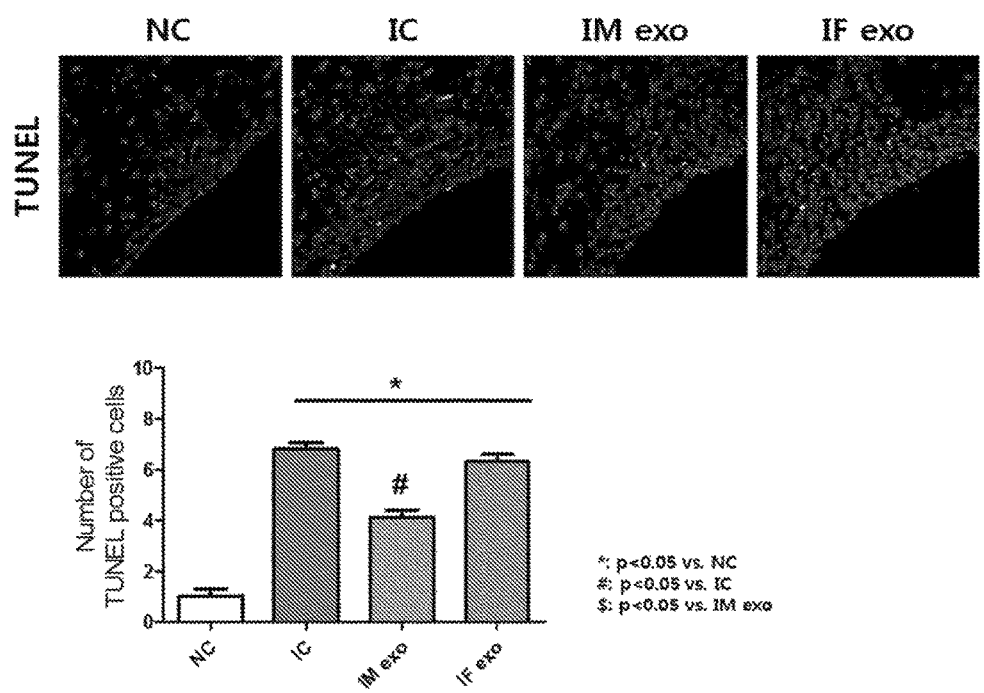
FIG. 12 illustrates TUNEL assay results in brain tissues of intraventricular hemorrhage animal models.

As illustrated in FIG. 12, it can be confirmed that the number of TUNEL-positive cells in the IVH-induced group greatly increases compared to the normal group. But, the group, to which the mesenchymal stem cell-derived exosomes were administrated, shows a TUNEL-positive cell number statistically, significant low compared to the IVH-induced group and the group to which the fibroblast-derived exosomes were administrated. From these results, it can be confirmed that the mesenchymal stem cell-derived exosomes have inhibition effects on brain cell death increased by intraventricular hemorrhage.

3-5. Reactive Gnosis Analysis

To analyze a reactive gliosis degree, brain tissue specimens obtained in the same manner as in Examples 3 and 4 were subjected to immunohistochemistry analysis with anti-GFAP (neuronal specific glial fibrillary acidic protein) antibody (rabbit polyclonal, Dako, Glostrup, Denmark; 1:1000 dilution) according to a conventionally known method. Results are illustrated in FIG. 13.

Figure 13:
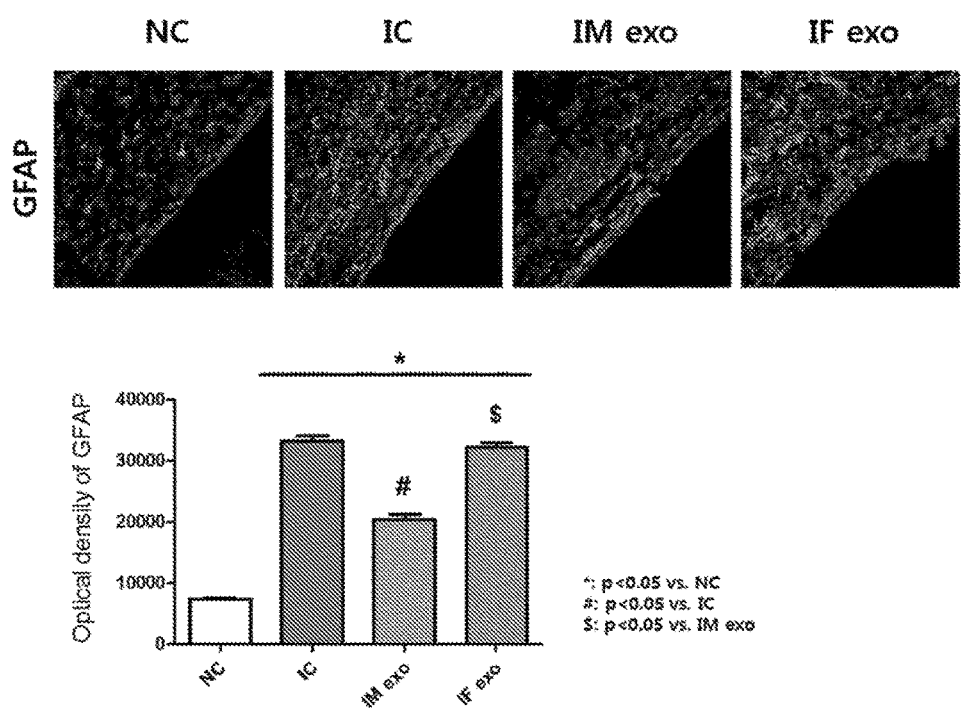
FIG. 13 illustrates immunohistochemical staining results using anti-GFAP antibody in brain tissues of intraventricular hemorrhage animal models.

As illustrated in FIG. 13, a GFAP staining degree of the IVH-induced group is higher than the normal group. But, a GFAP staining degree of the group, to which the mesenchymal stem cell-derived exosomes were administrated, is statistically, significantly low compared to the IVH-induced group and the group to which the fibroblast-derived exosomes were administrated. From these results, it can be confirmed that the mesenchymal stem cell-derived exosomes reduce the reactive gliosis increased by intraventricular hemorrhage.

3-6. Activated Microglia Analysis

To analyze activated microglia characteristically observed in brain inflammation, brain tissue specimens obtained in the same manner as in Examples 3 and 4 were subjected to immunohistochemistry analysis with anti-ED-1 antibody (mouse monoclonal, Millipore, Concord Road, Mass., USA; 1:100 dilution). Results are illustrated in FIG. 14.

Figure 14:
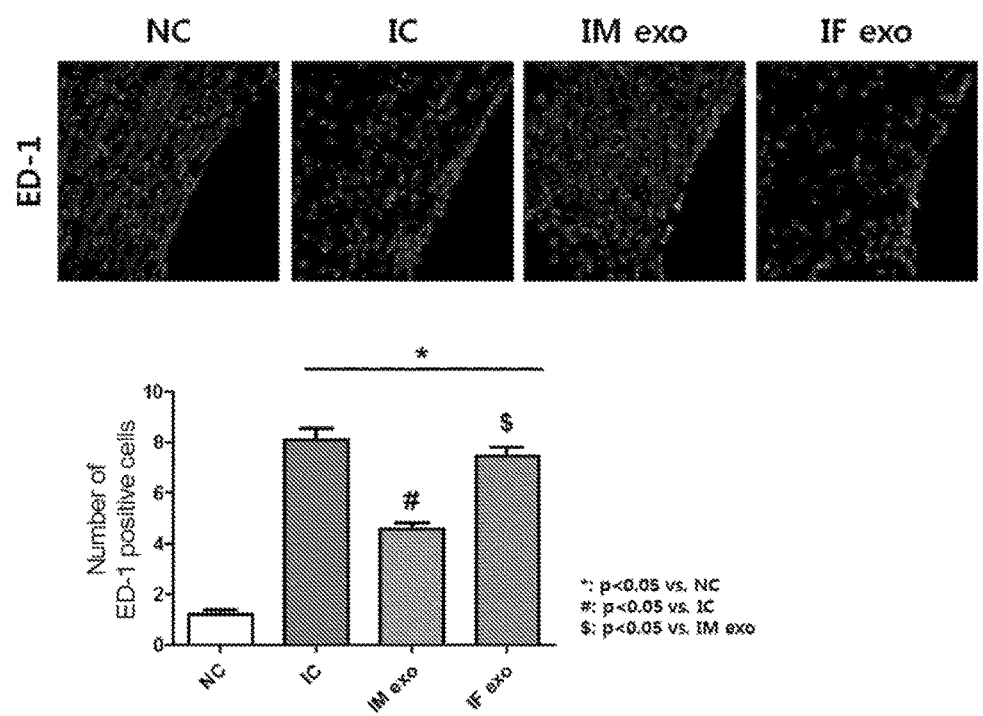
FIG. 14 illustrates immunohistochemical staining results using anti-ED-1 antibody in brain tissues of intraventricular hemorrhage animal models.

As illustrated in FIG. 14, it can be confirmed that an ED-1-positive cell number of the IVH-induced group is greatly increased compared to the normal group. But, a ED-1-positive cell number of the group, to which the mesenchymal stem cell-derived exosomes were administrated, is statistically, significantly small compared to the IVH-induced group and the group to which the fibroblast-derived exosomes were administrated. From these results, it can be confirmed that the mesenchymal stem cell-derived exosomes reduce cellular inflammation increased by intraventricular hemorrhage.

3-7. Myelination Analysis

To analyze a myelination degree, brain tissue specimens obtained in the same manner as in Examples 3 and 4 were subjected to immunohistochemistry analysis with anti-MBP (myelin basic protein) antibody (rabbit polyclonal, Abcam, Cambridge, Mass., USA; 1:1000 dilution). Results are illustrated in FIG. 15.

Figure 15:
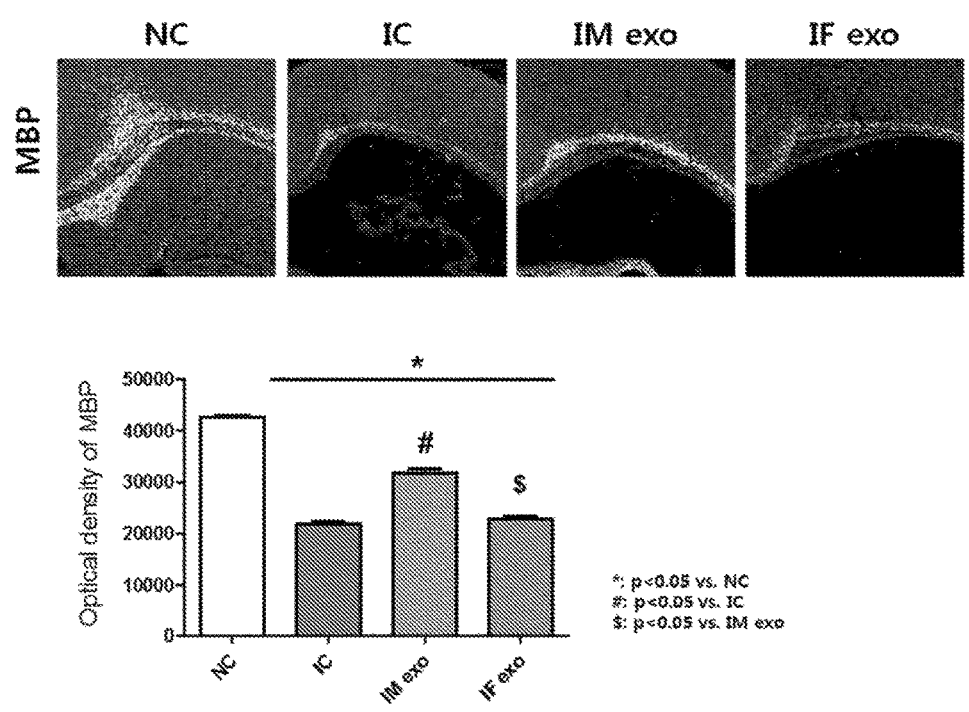
FIG. 15 illustrates immunohistochemical staining results using anti-MBP antibody in brain tissues of intraventricular hemorrhage animal models.

As illustrated in FIG. 15, it can be confirmed that an MBP staining degree of the IVH-induced group is low compared to the normal group. But, an MBP staining degree of the group, to which the mesenchymal stem cell-derived exosomes were administrated, is statistically, significantly high compared to the IVH-induced group and the group to which the fibroblast-derived exosomes were administrated. From these results, it can be confirmed that the mesenchymal stem cell-derived exosomes improve the myelination damaged and decreased by intraventricular hemorrhage.

3-8. Inflammatory Cytokine Analysis

The concentrations of IL (interleukin)-1α, IL-1β, IL-6, and TNF (tumor necrosis factor)-α, as inflammatory cytokines, were measured in homogenous brain tissue suspensions using a Milliplex MAP ELISA Kit (Millipore, Billerica, Mass.). Results are illustrated in FIG. 16.

Figure 16:
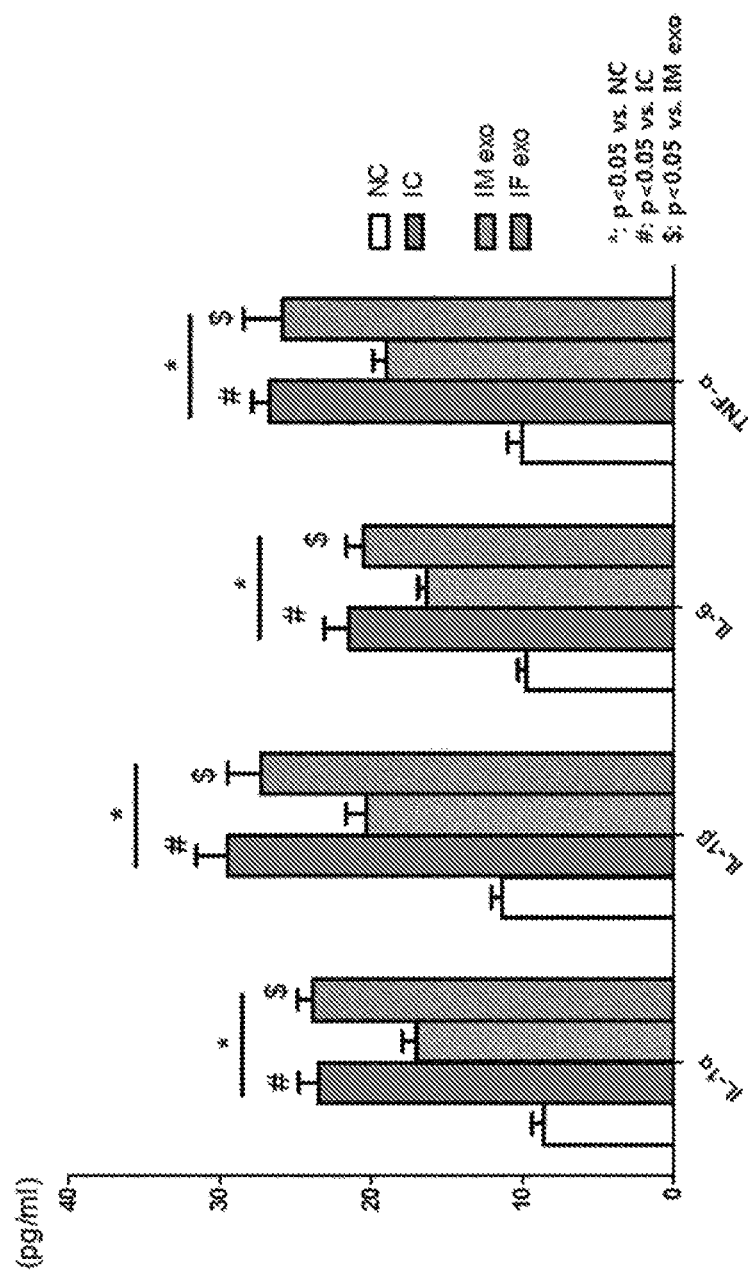
FIG. 16 illustrates results of measuring the concentrations of inflammatory cytokines (IL-1$\alpha$, IL-1$\beta$, IL-6 and TNF-$\alpha$) in brain tissues of intraventricular hemorrhage animal models using ELISA.

As illustrated in FIG. 16, it can be confirmed that the concentrations of the inflammatory cytokines in the IVH-induced group are high compared to the normal group. But, the concentrations of the inflammatory cytokines in the group, to which the mesenchymal stem cell-derived exosomes were administrated, are statistically, significantly low compared to the IVH-induced group and the group to which the fibroblast-derived exosomes were administrated. From these results, it can be confirmed that the mesenchymal stem cell-derived exosomes reduces inflammation increased by intraventricular hemorrhage.

From the aforementioned experimental results, it can be confirmed that the stem cell-derived exosome according to the present invention has remarkable nerve cell protective effects such as the inhibition of ventricular enlargement in an intraventricular hemorrhage (IVH) animal model, decrease in hydrocephalus, and inhibition of nerve cell death and inflammatory cells, and thus can be useful in treating cerebrovascular diseases including IVH and the like.

INDUSTRIAL APPLICABILITY

The stem cell-derived exosomes according to the present invention have superior nerve cell protective effects, such as inhibition of cerebral ventricular distention, reduction of hydrocephalus, and inhibition of nerve cell death and cellular inflammation in an intraventricular hemorrhage (IVH) animal model, and thus, can be useful in treating cerebrovascular diseases including intraventricular hemorrhage, etc.

What is claimed is:

1. A method for treating a cerebrovascular disease, comprising:
 administering to a subject having the cerebrovascular disease an effective amount of exosome derived from a stem cell,
 wherein the cerebrovascular disease is intraventricular hemorrhage (IVH), and
 wherein the stem cell is a mesenchymal stem cell.

2. The method according to claim 1, wherein the mesenchymal stem cell is derived from one or more tissues selected from the group consisting of umbilical cord, cord blood, bone marrow, fat, muscle, nerve, skin, amnion, and placenta.

3. The method according to claim 1, wherein the stem cell is treated with thrombin.

4. The method according to claim 1, wherein the exosome is administered in a pharmaceutical composition containing a pharmaceutically acceptable carrier.

5. The method according to claim 4, wherein the pharmaceutical composition is administered by injection or spray.

* * * * *